United States Patent
Paetz et al.

(10) Patent No.: US 9,428,484 B2
(45) Date of Patent: Aug. 30, 2016

(54) METHOD FOR THE PRODUCTION OF CYCLIC DIESTERS, IN PARTICULAR DILACTIDE

(71) Applicant: UHDE INVENTA-FISCHER GMBH, Berlin (DE)

(72) Inventors: Caspar Paetz, Berlin (DE); Udo Muehlbauer, Berlin (DE); Habib Driouch, Leipzig (DE)

(73) Assignee: UHDE INVENTA-FISCHER GMBH, Berlin (DE)

( * ) Notice: Subject to any disclaimer, the term of this patent is extended or adjusted under 35 U.S.C. 154(b) by 0 days.

(21) Appl. No.: 14/435,640

(22) PCT Filed: Oct. 23, 2013

(86) PCT No.: PCT/EP2013/072188
§ 371 (c)(1),
(2) Date: Apr. 14, 2015

(87) PCT Pub. No.: WO2014/064160
PCT Pub. Date: May 1, 2014

(65) Prior Publication Data
US 2015/0266849 A1    Sep. 24, 2015

(30) Foreign Application Priority Data
Oct. 26, 2012 (EP) .................................... 12190199

(51) Int. Cl.
C07D 319/06 (2006.01)
C07D 319/12 (2006.01)

(52) U.S. Cl.
CPC .................................. C07D 319/12 (2013.01)

(58) Field of Classification Search
CPC ............................... C07D 31/06; C08G 63/08
USPC ........................................................ 549/274
See application file for complete search history.

(56) References Cited

U.S. PATENT DOCUMENTS

| | | | |
|---|---|---|---|
| 2,526,554 A | 10/1950 | Gresham et al. | |
| 5,229,528 A | 7/1993 | Brake et al. | |
| 5,420,304 A * | 5/1995 | Verser et al. | 549/274 |
| 5,502,215 A | 3/1996 | Yamaguchi et al. | |
| 5,728,847 A | 3/1998 | Ohara et al. | |
| 6,229,046 B1 | 5/2001 | Eyal et al. | |
| 6,320,077 B1 | 11/2001 | Eyal et al. | |
| 6,534,679 B2 | 3/2003 | Eyal et al. | |
| 6,875,839 B2 | 4/2005 | Gerking et al. | |
| 7,144,977 B2 | 12/2006 | Eyal et al. | |
| 7,557,224 B2 | 7/2009 | Nishida et al. | |
| 8,053,584 B2 | 11/2011 | Meerdink et al. | |
| 8,431,683 B2 | 4/2013 | Coszach et al. | |
| 8,481,675 B2 | 7/2013 | Coszach et al. | |
| 8,592,609 B2 | 11/2013 | Coszach et al. | |
| 8,614,338 B2 | 12/2013 | Coszach et al. | |
| 2002/0004611 A1 | 1/2002 | Eyal et al. | |
| 2003/0158360 A1 | 8/2003 | Gerking et al. | |
| 2003/0176736 A1 | 9/2003 | Eyal et al. | |
| 2004/0210088 A1 | 10/2004 | Eyal et al. | |
| 2008/0234500 A1 | 9/2008 | Meerdink et al. | |
| 2011/0155557 A1 | 6/2011 | Coszach et al. | |
| 2012/0029228 A1 | 2/2012 | Coszach et al. | |
| 2012/0142958 A1 | 6/2012 | Coszach et al. | |
| 2012/0165554 A1 | 6/2012 | Coszach et al. | |

FOREIGN PATENT DOCUMENTS

| | | | | |
|---|---|---|---|---|
| CN | 101434594 A | 5/2009 | | |
| CN | 101903370 A | 12/2010 | | |
| CN | 101906041 A | 12/2010 | | |
| DE | 196 37 404 A1 | 3/1997 | | |
| DE | 694 05 201 T2 | 1/1998 | | |
| DE | 698 15 369 T2 | 5/2004 | | |
| DE | 603 17 581 T2 | 9/2008 | | |
| EP | 0 628 533 A1 | 12/1994 | | |
| EP | 0 657 447 B1 | 8/1997 | | |
| EP | 0 893 462 A2 | 1/1999 | | |
| EP | 0893462 * | 1/1999 | ............ | C08G 63/08 |
| EP | 1 276 890 B1 | 1/2008 | | |
| WO | WO 2010/118954 A1 | 10/2010 | | |
| WO | WO 2010/118955 A1 | 10/2010 | | |
| WO | WO 2011/029648 A1 | 3/2011 | | |
| WO | WO 2011/104728 A1 | 9/2011 | | |

OTHER PUBLICATIONS

European Patent Office, International Search Report in International Application No. PCT/EP2013/072188 (Dec. 6, 2013).
European Patent Office, Written Opinion in International Application No. PCT/EP2013/072188 (Dec. 6, 2013).
International Bureau of WIPO, International Preliminary Report on Patentability in International Application No. PCT/EP2013/072188 (Apr. 28, 2015).
Faisal et al., "Depolymerization of Poly (L-lactic acid) under Hydrothermal Conditions," *Asian Journal of Chemistry*, vol. 19, No. 3, pp. 1714-1722 (2007).
Yagihashi et al., "Recovery of l-Lactic Acid from Poly(l-lactic acid) under Hydrothermal Conditions of Dilute Aqueous Sodium Hydroxide Solution," *Ind. Eng. Chem. Res.*, 49(3):1247-1251 (2010).
State Intellectual Property Office of the People'S Republic of China, Notification of the First Office Action in Chinese Patent Application No. 201380055877.4 (Mar. 22, 2016).

* cited by examiner

*Primary Examiner* — Nizal Chandrakumar
(74) *Attorney, Agent, or Firm* — Leydig, Voit & Mayer, Ltd.

(57) ABSTRACT

The present invention relates to a method for the production of cyclic carboxylic acid esters, in particular intramolecular lactones, such as e.g. dilactide, the production of these cyclic esters from oligomeric carboxylic acids being effected by cyclizing depolymerization. During this reaction, a condensation product of these oligomeric carboxylic acids is produced as by-product, i.e. a mixture of higher-molecular oligomeric carboxylic acids which are hydrolyzed in a further step and hence recovered. This hydrolysate can be added again to the cyclizing depolymerization which is implemented in the first step.

15 Claims, 1 Drawing Sheet

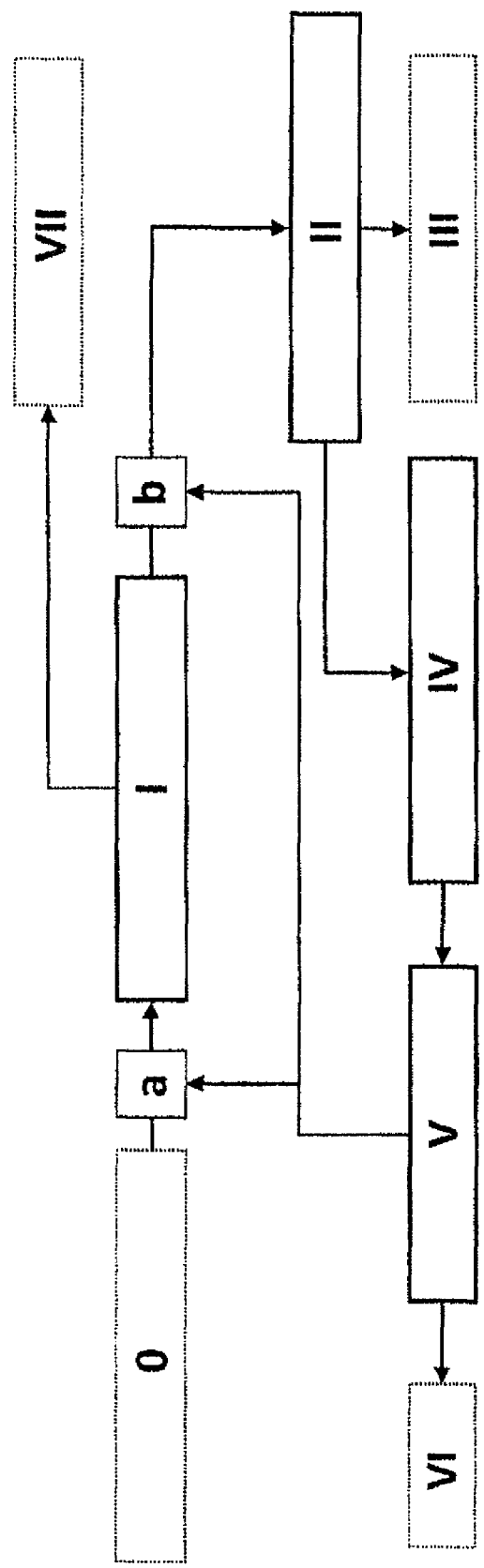

METHOD FOR THE PRODUCTION OF CYCLIC DIESTERS, IN PARTICULAR DILACTIDE

CROSS-REFERENCE TO RELATED APPLICATIONS

This patent application is the U.S. national phase of International Application No. PCT/EP2013/072188, filed on Oct. 23, 2013, which claims the benefit of European Patent Application No. 12190199.5, filed Oct. 26, 2012, the disclosures of which are incorporated by reference in their entireties for all purposes.

The present invention relates to a method for the production of cyclic carboxylic acid esters, in particular intramolecular lactones, such as e.g. dilactide, the production of these cyclic esters from oligomeric carboxylic acids being effected by cyclising depolymerisation. During this reaction, a condensation product of these oligomeric carboxylic acids is produced as by-product, i.e. a mixture of higher-molecular oligomeric carboxylic acids which are hydrolysed in a further step and hence recovered. This hydrolysate can be added again to the cyclising depolymerisation which is implemented in the first step.

All common methods at present for the production of PLA on an industrial scale are based on ring-opening polymerisation of dilactide. The production of the dilactide is effected for this purpose by the cyclising depolymerisation of lactic acid polycondensate. A lactic acid polycondensate with a low average molecular weight (500 . . . 2000 Da) is thereby heated at low pressure with addition of a catalyst, as a result of which the dilactide is formed and withdrawn in vaporous form. A residue is thereby necessarily left over, which consists of the catalyst, a lactic acid polycondensate with an average molecular weight of 3000 . . . 5000 Da and various impurities. The quantity of residue has a direct influence on the total yield of the method. There is therefore a tendency to convert the lactic acid polycondensate as completely as possible to form dilactide in order to increase the yield.

A peculiarity of the PLA production resides in the fact that lactic acid is present in two optically active forms, the S(+)- and the R(−) form which are also termed L- and D-lactic acid. In the production of dilactide, three optically different forms can correspondingly be formed, L-lactide (with absolute S,S-configuration of the stereocentres), meso-lactide (with an absolute R,S-configuration of the stereocentres) and D-lactide with an absolute R,R-configuration of the stereocentres). Primarily, L-lactide is desired, which is also formed predominantly since generally the lactic acid used comprises up to >99% of L-isomers.

However, in all steps of the method, the result can basically be conversion of L-lactic acid into D-lactic acid or of L-lactide into meso-lactide and D-lactide (racemisation). It is disadvantageous for the total yield of the method that, during conversions above the normal 95%, the degree of racemisation of L-lactide into meso-lactide greatly increases. Hence the additional yield is achieved at the cost of a high-quality product since only L-lactide with a proportion of at most 10 . . . 12% meso-lactide can be polymerised to form a polymer with a high melting point.

In the previous state of the art, comprehensive information relating to the hydrolysis of PLA or lactic acid polycondensate (also: lactic acid oligomers) is present. There are included herein, e.g. WO2011/029648, WO2010/11894, U.S. Pat. No. 5,229,528, EP0628533 or EP0893462. Likewise, possibilities for further increasing the conversion have been published, e.g. DE19637404 or U.S. Pat. No. 7,557,224. At increased temperatures, with the addition of a racemisation inhibitor, the residue is reduced as far as possible without the racemisation increasing too greatly. In the previous state of the art, also comprehensive information with respect to the purification of lactic acid and the recovery of lactide is present; DE 19637 404 A1, DE 60317581 T2, DE 69405201 T2 (EP 0657447 B1), DE 69815369 T2, EP 1276890 B1, US2011/0155557 A1. In the polymerisation of lactic acid, one or more catalysts which are supplied to the polymerisation reactor are known. That can include metals or inorganic/organic metal compounds, such as e.g. Sn—, Zn— or Fe compounds (DE 19637 404 A1, DE 60317581 T2, DE 60317581 T2).

However, there is no known source in the case of which the reduction in racemisation during depolymerisation with hydrolysis of the residue and subsequent recycling into the process is described. Also no data about catalyst removal or -recovery are described.

WO2011/029648 and WO2010/118954 (Galactic): the use of ethyllactate as hydrolysis medium for the degradation of PLA is described therein. The production of ethanol which must be distilled off subsequent to the hydrolysis is disadvantageous.

WO2010/118955 (Galactic): the alcoholysis with various lactates as hydrolysis medium is described therein, the respective alcohol here must also be removed later.

U.S. Pat. No. 2,526,554: early mention of alcoholysis. However only for polyesters made of beta-lactones.

U.S. Pat. No. 5,229,528: hydrolysis of PHA (to which PLA also belongs) with water at increased pressure and increased temperature. The hydrolysis in the closed vessel is disadvantageous, in addition, the method is discontinuous. In addition, very long reaction times are required since pure water is used as hydrolysis medium.

EP0628533 (DuPont): description of the hydrolysis by water, alcohols, amines, diamines and mixtures thereof. Includes separation of the hydrolysate in the $1^{st}$ claim.

EP0893462 (Cargill): in this patent (example 4), the hydrolysis of the depolymerisation residues with 88% lactic acid is described. It is thereby disadvantageous that no catalyst removal takes place and that hence a constantly increasing portion of D-isomers can be produced due to concentration thereof.

Faisal 2007 (Asian Journal of Chemistry vol. 19, no. 3, 1714-1722): the hydrolysis of PLA at high temperatures (>160° C.) is described there. In fact this high temperature level is thereby disadvantageous because racemisation can thereby take place to a greater extent.

Yagihashi 2010 (Ind. Eng. Chem. Res., 2010, 49 (3), pp. 1274-1251): diluted sodium hydroxide solution is used there in the temperature range of 70-180° C. No racemisation within 20-60 min reaction time. The necessity for subsequent removal of the sodium is disadvantageous.

U.S. Pat. No. 7,557,224 (Kyushi Institute of Technology): the selective pyrolysis of polycondensate with the addition of aluminium hydroxide is described. The extremely high temperature of above 300° C. is disadvantageous.

DE 19637404: the direct recovery of lactide from PLA is described, however this occurs only with a huge catalyst use and at very high temperatures.

Fan 2003 (Green Chemistry, 2003, 5, 575-579): pyrolysis of the depolymerisation residue at 250 . . . 300° C. with the addition of calcium components in order to prevent excessive racemisation.

DE 19637 404 A1 (Schimadzu Corp): a method for recovery of lactide from polylactic acid (PLA), comprising the heat treatment of a PLA, is described.

DE 60317581 T2 (Tate & Lyle plc): the patent relates to a method for purifying dilactide from a vaporous crude dilactide product stream which comprises at least the dilactide, lactic acid, water and linear lactic acid oligomers.

DE 69405201 T2 (EP 0657447 B1) (Musashino Chemical Laboratory Ltd): a method for purification of dilactide is described therein.

DE 69815369 T2 (Cargill): the invention relates to the processing of lactic acid, in particular the separation of lactic acid flows and lactide salt flows from mixtures, the isolation and processing of lactic acid and the isolation of the lactate salt in preferred forms.

EP 1276890 B1 (Uhde Inventa-Fischer GmbH): the invention relates to a method for the production of polylactic acid (PLA) from lactic acid produced by fermentation, starch being used as raw material.

US 2011/0155557 A1 (Futerro): the invention relates to a method for the production of lactide from lactic acid.

Within the scope of the present application, the following definitions are used:

Carboxyl End Groups of the PLA Hydrolysate, Molar Mass of the PLA Oligomers:

The PLA oligomer is dissolved in acetone. After the addition of methanol, the solution is titrated with 0.1 N benzyl alcoholic KOH solution. The end point is detected potentiometrically. From the carboxyl end group concentration ("COOH"), measured in mmol/kg, the number average of the molar mass can be calculated according to the equation $Mn=10^6/COOH$.

Carboxyl Groups in the Lactide:

The dilactide sample is dissolved in methanol and subsequently titrated in the same way as in the carboxyl end group determination in the PLA oligomer.

Optical Isomers of the Dilactide:

The dilactide sample is dissolved in a mixture of 90/10 ml/ml n-hexane/ethanol. The dissolved components are separated by HPLC on a chiral column and analysed with a UV detector at 223 nm.

D Proportion in Lactic Acid and PLA:

A sample of PLA or of a PLA oligomer is hydrolysed with 1-N sodium hydroxide solution boiling at reflux and is neutralised after cooling. The neutralised sample is mixed with 3 millimolar copper sulphate solution in the ratio 19 ml/ml and separated with HPLC on a stereospecific column into the components which are subsequently analysed with a UV detector at a wavelength of 238 nm. A lactic acid sample is dissolved directly in the 3 millimolar copper sulphate solution and analysed with HPLC as described.

Dilactide:

Cyclic ester of 2 lactic acid molecules which can occur in the form of pure L-lactide (S,S-lactide), D-lactide (R,R-lactide) or meso-lactide (S,R-lactide) or (in most cases) in the form of a mixture of at least two of these components. The cyclising depolymerisation produces crude dilactide which, in addition to the mentioned isomers of lactide, can also comprise linear oligomers, higher cyclic oligomers and residues of lactic acid and water. There should be understood by L-lactide, the cyclic ester of two L-lactic acid units, by D-lactide, the cyclic ester of two D-lactic acid units, by meso-lactide, the cyclic ester of a D- and of an L-lactic acid unit. Racemic lactide (rac-lactide) is a 1:1 mixture of L- and D-lactide.

The term racemisation in this context describes the conversion of L-into D-units and vice versa. Since this process starts however with L-lactic acid, there is always meant, according to the invention, by an increasing racemisation, the increased formation of D-units. Because of the differing stability of the chiral centres of lactic acid and dilactide, this racemisation takes place significantly more easily with dilactide.

Cyclising Depolymerisation:

This reaction is the reverse reaction of ring-opening polymerisation which is used in almost all industrial processes for forming the PLA from lactide. It is undesired in the finished PLA because, during processing, it leads to molar mass decomposition and hence to impairment in the product properties. It is used in the production of dilactide in order to produce a crude dilactide from the oligomer obtained by polycondensation of the lactic acid, which crude dilactide forms the starting substance for the ring-opening polymerisation after purification. Crude dilactide comprises, in addition to 80 . . . 90% dilactide, also residues of water, lactic acid, short-chain lactic acid oligomers and also traces of other impurities (e.g. organic acids).

The theoretically maximum possible yield in this process is 80%, i.e. 1 kg dilactide is formed from 1.25 kg lactic acid. The yields indicated according to the invention relate to this maximum possible state. A total yield of 95% therefore describes a process in which 0.95 kg dilactide has been produced from 1.25 kg lactic acid. Since the lactic acid converted by evaporation into the crude dilactide fraction can be separated and returned at a later time in the method, a total yield of 95% and more is thus achievable, according to the invention, with a crude dilactide which comprises 80% dilactide.

Polylactide (PLA):

Polymer from lactic acid units, e.g. produced by ring-opening polymerisation of the L-, D- or meso-lactide or a mixture of two or three of these lactides. This can also concern a mixture of polymers from the mentioned pure or mixed lactides. PLA generally has a number average molecular weight >10,000 g/mol. The quality of the PLA which is produced from dilactide depends upon the content thereof of D-lactide and meso-lactide units. With an increasing content of D-lactic acid units in the PLA formed predominantly from L-lactide units, the melting point, thermal dimensional stability, crystallisation rate and also crystallisation degree thereof drop. If this content of D,D-units in the PLA exceeds 6% (corresponds to 12% meso-lactide since this only comprises one D-unit) the polymer is amorphous, the melting point coincides with the glass transition temperature of e.g. 55° C. The same applies for meso-lactide and L-lactide in a PLA constructed predominantly from D-units.

Hydrolysing Medium:

According to the invention, there should be understood thereby, water, lactic acid or a mixture of water and lactic acid. Pure lactic acid in fact does not cause hydrolysis with PLA but reesterification. The effect—the decomposition into PLA oligomers—is however the same as with hydrolysis. A differentiation is therefore superfluous for the purposes of this invention. Lactic acid always contains water however in industrially available qualities and promotes hydrolysis catalytically.

The term "lactic acid" used according to the invention hence includes small proportions of water. Also other water-containing acids promote hydrolysis but must be removed subsequently from the product since they disturb the depolymerisation into lactide or the polymerisation thereof into PLA differently from lactic acid.

Partial Hydrolysis:

Like all polyesters, PLA is also amenable to hydrolytic cleavage of the polymer chains. What must be avoided during polymerisation and processing is made use of in the method according to the invention for the purpose of decomposing the polymer specifically to a desired molar mass. Although the hydrolysis of PLA takes place in fact at temperatures below the melting point, the dwell times required for this or the necessary water concentration in the polymer are very high. A technical process is advantageous if it reaches the objective within short dwell times, which leads to small constructional sizes in the apparatus. The process according to the invention uses, in addition, the smallest possible quantity of water for the hydrolysis, in the aim of only achieving the desired molar mass exactly. Hence excess water is avoided, which must be removed again after conclusion of the hydrolysis reaction with expenditure on energy and apparatus. Hydrolysis with a significantly greater quantity of water leads furthermore to greater partial racemisation (JP 2009-249508; M. Faisal et al, Asian Journal of Chemistry vol. 19, no. 3 (2007), p. 1714).

Sn Precipitation, Filtration/Centrifugation and H$_2$S Removal:

In a first step of processing of the hydrolysate, the tin catalyst is precipitated from the hydrolysate by addition of precipitant at room temperature with gentle agitation. The precipitate is removed by filtration. The filtrate subsequently comprises only a few ppm tin.

During the hydrolysate treatment with precipitant, hydrogen sulphide (H$_2$S) is produced. This can be removed by increasing the temperature to 40° C. with agitation. The precipitated tin can be used for the synthesis of Sn oxide and then be reused as catalyst for the dilactide polymerisation.

Nanofiltration:

After the Sn precipitation and the Sn—H$_2$S removal, the now low-tin solution is subsequently supplied for nanofiltration (NF).

This is a pressure-driven membrane method which retains particles or ions in the nanometer range (approx. 1-10 nm), such as heavy metal ions. Furthermore, colourants can also be retained by the NF. Following the nanofiltration (NF) is the polishing, the final purification, of the lactic acid. The aim here is to free the lactic acid of all remaining impurities including colourants. During the polishing (ion exchange first step and second step), the lactic acid is concentrated gradually by evaporation. At the end of the purification step, the LA polymer quality should be achieved so that it can be supplied here to the polymerisation.

Ion Exchange:

The use of ion exchangers is an essential component of processing of the hydrolysate and is termed polishing. Ion exchangers, as used today, are not soluble in water but are swellable synthetic resins with substituted ion-active groups. Hence, they represent electrolytes in solid form. Ions of a specific type can diffuse out of the aqueous phase into the water-containing exchanger phase and are exchanged at the exchange-active groups for equally-charged ions in an equivalent quantity.

On the basis of the described high significance of monomers with as high as possible an optical purity for the production of polylactides, it is hence the object of the present invention to indicate a method for the production of cyclic esters, in particular dilactide, with which the dilactide can be obtained with as high a yield as possible and with as high an optical purity as possible.

This object is achieved by the features of patent claim 1. The dependent patent claims thereby represent advantageous developments.

According to the present invention, a method for the production of cyclic esters of general formula I

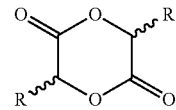

Formula I is hence provided, in which a) in a first step, a part of a mixture of oligomeric carboxylic acids of formula II

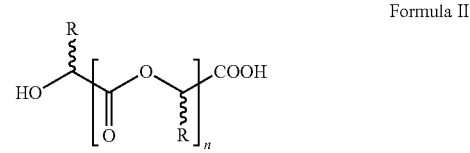

Formula II respectively R being selected, in formulae I to II, from linear or branched aliphatic radicals with 1 to 6 carbon atoms and, in formula II, the average value for n being between 2 and 40, is converted by cyclising depolymerisation into the cyclic diester of general formula I and the thereby produced cyclic diester of general formula I is separated, the part of the oligomeric carboxylic acid of formula II, which is not converted into the cyclic diester of general formula I, is made to react to form a residue during the cyclising depolymerisation, which residue comprises a mixture of oligomeric carboxylic acids of formula II with a higher average value for n than the mixture of oligomeric carboxylic acids of formula II fed into the first step, b) in a second step, the residue, obtained in the first step, of a mixture of oligomeric carboxylic acids of formula II, the average value for n being between 1 and 20, is hydrolysed to form an alpha-hydroxycarboxylic acid of formula III

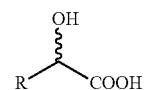

or a mixture of oligomeric carboxylic acids of formula II with an average value for n between 1 and 20 and an alpha-hydroxycarboxylic acid of formula III, and the hydrolysate obtained in the second step is fed at least partially or completely into the first step.

According to the invention, it is now provided to limit the depolymerisation conversion in the first step, i.e. the cyclising depolymerisation of the first step is only implemented until at most 98% by weight of the mixture of oligomeric carboxylic acids of formula II, which is used, is converted by the cyclising depolymerisation into the cyclic diester of general formula I.

Surprisingly, it was able to be established that, with such a mode of operation, the yield of a method for the production of cyclic diesters can be significantly increased without thereby increasing the racemisation rate and hence reducing the achievable product quality. With the method according to the invention, total yields of up to >99% with simultaneously acceptable racemisation are possible. The essential idea thereby is that a new mode of operation for the step of depolymerisation is combined with a processing method for the residue and the conversion in the first step is limited. As a result of the altered mode of operation of depolymerisation, the racemisation is reduced, however the residue quantity is increased at the same time. By recycling the residue into a preceding process step after processing by hydrolysis and possibly necessary purification steps (filtration, precipitation, ion exchange), the total yield of the process is significantly increased, possibly the thereby achieved degree of racemisation being at most as high as without this method step, with a tendency to be even lower.

According to a preferred embodiment of the method according to the invention, the mixture of oligomeric carboxylic acids of formula II, fed into the first step, is obtained by a preceding polycondensation of an alpha-hydroxycarboxylic acid of formula III

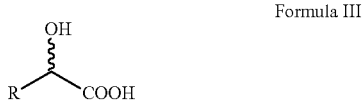

Formula III

R having the above-indicated meaning. According to this advantageous variant, the mixture of oligomeric carboxylic acids of formula II, which are used for the first step of the method according to the invention for the production of cyclic esters, is thereby produced directly by polycondensation of the corresponding alpha-hydroxycarboxylic acid of formula III. This polycondensation of the alpha-hydroxycarboxylic acids of formula III can thereby be produced directly for example in situ in a preceding reactor, the thereby produced mixture of oligomeric carboxylic acids of formula II can be used directly for the further cyclising depolymerisation. Hence no separation or processing of the oligomeric carboxylic acids of formula II which are produced in this method variant is necessary.

Furthermore, it is preferred if, alternatively or additionally to feeding the hydrolysate into the first step, the hydrolysate is fed partially or completely into the preceding polycondensation of the alpha-hydroxycarboxylic acid of formula III. According to this method variant, the hydrolysate occurring in the second step of the method according to the invention can be also fed directly into the preceding polycondensation step of the alpha-hydroxycarboxylic acid of formula III. In the case where the hydrolysate comprises an alpha-hydroxycarboxylic acid of formula III, this can be condensed there again to form oligomeric carboxylic acids, possibly contained low-molecular oligomeric carboxylic acids of formula II can be further condensed for example. In every case, such a method variant is distinguished by a high material economy of the educts used since the reaction components not converted into the cyclic ester according to formula I can be reused in a circulation by being fed again into the corresponding reaction steps.

In particular, it is advantageous if the cyclising depolymerisation of the first step is implemented until at most 95% by weight, preferably from 50 to 95% by weight, particularly preferred from 60 to 85% by weight, of the mixture of oligomeric carboxylic acids of formula II, which is used, is converted by the cyclising depolymerisation into the cyclic diester of general formula I. By means of such a method management, a racemisation can be avoided to the greatest possible extent during the cyclising depolymerisation, i.e. a change in the absolute stereo configuration of the respective stereocentres takes place in the oligomeric carboxylic acids of formula II. By means of hydrolysis and recycling of the non-converted residue, the total yield of this method is in addition not impaired so that an extremely advantageous economic mode of operation results.

A further advantageous embodiment of the method according to the invention provides that the partial hydrolysis of the residue implemented in the second step is implemented by conversion of the residue with a hydrolysing medium, selected from the group consisting of water, an alpha-hydroxycarboxylic acid of formula III or mixtures of water and an alpha-hydroxycarboxylic acid of formula III with a preferred water content of 1 to 99% by weight, preferably 10 to 80%, particularly preferred 20 to 60%.

A further preferred variant provides that the partial hydrolysis implemented in the second step is implemented at pressures between 500 mbar and 2 bar, preferably at 900 mbar to 1,100 mbar and/or at temperatures between 50 and 300° C., preferably between 80 and 120° C.

In addition, it is preferred to implement purification of the hydrolysate before recycling into the first step and/or the polycondensation preceding the first step. In particular, such a purification is effected by filtration, nanofiltration, centrifugation, distillation, precipitation and/or separation of a possibly present catalyst, ion exchange method or a plurality of the previously mentioned purification methods.

The cyclising depolymerisation in the first step can be accelerated by using a catalyst, preferably a tin-containing catalyst, in particular tin-(IV)-octoate, in the first step.

Preferred temperatures in the cyclic depolymerisation implemented in the first step are thereby between 100 and 300° C., preferably between 150 and 250° C.

Furthermore, it is advantageous if the cyclising depolymerisation and/or separation of the cyclic diester of general formula I, produced in the first step, is implemented at pressures which are reduced relative to normal conditions, preferably at pressures between 0.1 and 500 mbar, further preferred between 10 and 100 mbar.

In particular, the present method is suitable for the production of optically active cyclic esters of general formula I, i.e. cyclic esters of formula I in the case of which R represents linear or branched aliphatic radicals with 1 to 6 carbon atoms. It is hereby particularly preferred if R=methyl, i.e. the cyclic diester according to formula I is dilactide.

It is hereby particularly preferred if the corresponding diesters have a stereoisomeric purity of at least 95%, preferably at least 98%, in particular at least 99%, i.e. the stereocentres in formula II have up to at least 95%, preferably up to at least 98%, particularly preferred up to at least 99%, S-configuration or R-configuration.

In the case where the stereocentres in formula II have up to at least 95%, preferably up to at least 98%, particularly preferred up to at least 99%, S-configuration, it is preferred if the cyclising depolymerisation of the first step is implemented until at most 10%, preferably at most 5%, particularly preferred at most 3%, of the separated cyclic diester of general formula I has R,S-configuration and/or R,R-configuration.

Alternatively, it is preferred that, if the stereocentres in formula II have up to at least 95%, preferably up to at least 98%, particularly preferred up to at least 99%, R-configuration, the cyclising depolymerisation of the first step is implemented until at most 10%, preferably at most 5%, particularly preferred at most 3%, of the separated cyclic diester of general formula I has R,S-configuration and/or S,S-configuration.

According to the previously mentioned preferred embodiments, it is hence advantageous to conduct the cyclising depolymerisation of the first step such that as low as possible a racemisation takes place. The stereoisomeric purity of the obtained and separated cyclic diester can be established for example via chiral HPLC chromatography in the manner known per se from the state of the art.

Alternatively to the previously mentioned embodiments, it is advantageous that, in the case of optically active cyclic esters of formula I, the hydrolysis implemented in the second step is implemented until a maximum racemisation of 10%, preferably at most 5%, particularly preferred at most 3%, relative to the stereocentres of the residue, is effected.

The present invention is explained in more detail with reference to the subsequent examples and embodiments without restricting the invention to the specifically illustrated parameters. The embodiments, given by way of example, relate in particular to the production of dilactide, however they can likewise be transferred to other cyclic diesters according to general formula I.

According to the invention, a method for increasing the yield in the production of dilactide is indicated in which, in a first step, the depolymerisation of lactic acid polycondensate is stopped during a conversion which is so low that a low, one-digit racemisation degree is set (indicated in % D-isomers, relative to the total quantity of lactic acid). The thereby occurring residue is hydrolysed with the help of aqueous lactic acid at increased temperature (approx. 95° C.) and slightly lowered pressure (900 . . . 950 mbar, in order to remove volatile components). The composition of the hydrolysing medium is thereby chosen such that the resulting hydrolysate has exactly the desired molecular weight in order to be recycled into a corresponding process step. Additives are possibly added to the hydrolysing medium in order to bind impurities. Possibly, by means of filtration, further precipitation or ion exchange, the quantity of impurities is subsequently reduced in order to prevent excessive concentration in the process. Accompanying this, a low quantity of the hydrolysate is discharged as purification flow (purge). The thereby resulting loss of lactic acid, relative to the total lactic acid used, is preferably less than 0.5%. The thus obtained polycondensate can be recycled directly into the depolymerisation or a preceding polycondensation step where it is mixed with the newly supplied polycondensate. As a result, the energy for evaporating the excess water is saved in addition, which makes the process more economical.

EXAMPLES

Example 1

100 g of a lactic acid polycondensate with an average molecular weight of 1,000 g/mol is heated in an oil bath after addition of 30 mg Sn(II)-octoate at 20 mbar (a) to 200° C. The resulting vapour phase is condensed out and comprises up to over 90% dilactide. After 3.5 hours, 95% of the polycondensate was converted into dilactide. The resulting residue has an average molecular weight of 3,000 g/mol and is converted at 120° C. into the solid state.

In the course of the experiment, a plurality of samples is taken from the resulting dilactide phase. Determination of the racemisation degree $X_R$ in the dilactide produces the results represented in Table 1.

TABLE 1

| Racemisation degree $X_R$ in the residue of the cyclising depolymerisation | | | | | | | |
|---|---|---|---|---|---|---|---|
| | Time [h] | | | | | | |
| | 0 | 1 | 1.5 | 2 | 2.5 | 3 | 3.5 |
| $X_R$ [% D] | 0.2 | 2.0 | 2.2 | 2.3 | 2.5 | 4.0 | 8.1 |

Example 2

100 g of a lactic acid polycondensate with an average molecular weight of 1,000 g/mol is heated in an oil bath after addition of 30 mg Sn(II)-octoate at 20 mbar (a) to 200° C. The resulting vapour phase is condensed out and comprises up to over 90% dilactide. The reaction is stopped after approx. 2.5 hours with 80% conversion by removing the vacuum and cooling to room temperature. The resulting residue has an average molecular weight of 2,000 g/mol and is converted at 115° C. into the solid state. The racemisation degree in the residue is at 2.5% D-units.

Example 3

Respectively 100 g of the residue of example 1 and example 2 is melted and heated in 100 g hydrolysis medium, an aqueous lactic acid solution with 50% by weight of lactic acid proportion, at 100° C. and atmospheric pressure for 4 hours with reflux. The resulting solution is filtered in order to remove solid material particles. The thus obtained, homogeneous solution has a lactic acid proportion of 88% by weight (residue 1) or 87% by weight (residue 2). The racemisation degree is 8% (residue 1) or 3% (residue 2).

Example 4

100 g of the residue of example 2 is melted and heated with 50 g hydrolysis medium, an aqueous lactic acid solution with 60% by weight of lactic acid, at 100° C. and atmospheric pressure for 4 hours with reflux. The resulting solution is filtered in order to remove solid material particles. The thus obtained, homogeneous solution has a lactic acid proportion of 92% by weight (determined via titration).

Example 5

100 g of the residue of example 2 is melted and heated with 50 g hydrolysis medium, an aqueous lactic solution with 95% by weight of lactic acid proportion, at 100° C. and atmospheric pressure for 4 hours with reflux. The resulting solution is filtered in order to remove solid material particles. The thus obtained, homogeneous solution has a lactic acid proportion of greater than 99% by weight. The average molecular weight of the solution is 300 g/mol.

Example 6

30 l of a hydrolysate (100 g/l lactic acid) is agitated for 30 min with the addition of 1.5 g/l sodium sulphide ($Na_2S$) at 25° C. and 50 rpm. The precipitate is removed by filtration (table 2). The filtrate is used for further processing.

TABLE 2

Tin in the filtrate of the hydrolysate before and after filtration

| | tin (mg/l) | lactic acid (g/l) |
|---|---|---|
| before addition of $Na_2S$ | 420 | 99.7 |
| after addition of $Na_2S$ | <2 | 99.4 |

Example 7

30 l of a hydrolysate (10% lactic acid) is agitated for 30 min with the addition of 1 g/l thioacetamide ($C_2H_5NS$) at 60° C. and 50 rpm. The precipitate is removed by centrifugation (table 3). The filtrate is used for further processing.

TABLE 3

Tin in the filtrate of the hydrolysate before and after centrifugation

| | tin (mg/l) | lactic acid (g/l) |
|---|---|---|
| before addition of $C_2H_5NS$ | 420 | 99.7 |
| after addition of $C_2H_5NS$ | <2 | 99.6 |

Example 8

The hydrolysate of example 5 is converted into dilactide corresponding to example 2. Under the same test conditions (temperature, pressure, catalyst quantity), after a reaction time of 4 h, a conversion is thereby produced (dilactide relative to the quantity of polycondensate used) of at least 90%.

Example 9

The hydrolysate of example 6 or 7 is mixed with a lactic acid polycondensate with an average molecular weight of 1,000 g/mol which corresponds to the lactic acid polycondensate used in example 1 so that the resulting mixture produces a lactic acid polycondensate with an average molecular weight of 500 g/mol. The resulting mixture is converted to form dilactide corresponding to example 1. After 4 h, a conversion into dilactide of at least 90% is thereby produced.

FIG. 1 shows a flow chart of a method according to the invention which is explained with reference to the example of the production of dilactide. The same method management is however implementable also with other cyclic diesters, such as for example glycolide etc. Lactic acid is added from a reservoir 0 via a switch, a T-piece or a pump a, to a polycondensation reactor I. A polycondensation of this lactic acid to form oligomeric lactic acids is effected herein. In addition, oligomeric lactic acids can possibly already be present in the reaction mixture. During the polycondensation, water VII is split off, which can be removed for example in vaporous form and/or at reduced pressure. The polycondensate obtained in step I which essentially consists of oligomeric lactic acids is supplied to a depolymerisation reactor II via a switch, a T-piece or a pump b. In the polymerisation reactor, a cyclising depolymerisation is implemented, crude dilactide III which is separated from the depolymerisation reactor II being produced. The residue remaining in the depolymerisation reactor after the cyclising depolymerisation corresponds essentially to oligomeric dicarboxylic acids which have however a higher polycondensation degree than the oligomeric dicarboxylic acids obtained from step I have. The oligomeric dicarboxylic acids remaining during depolymerisation are converted into a hydrolysis step IV, as hydrolysing medium, for example water or a mixture of water and lactic acid can be used. Possibly, processing V of the hydrolysate can take place subsequently, for example solid materials, in particular also contained catalysts, being able to be separated after possibly ensuing precipitation. The residue separated during the processing can be separated for example via a purging outlet (purge) VI. The hence processed hydrolysate can be added for example via the switch, T-pieces or pumps a and/or b to the respective flow of the individual compounds so that an effective circulation of the components is possible. In particular, it is advantageous with this closed circulation system that merely lactic acid is fed in and crude dilactide with a high yield and high optical property is obtained.

Overall Example 100 g of a lactic acid polycondensate with an average molecular weight of 1,000 g/mol is heated to 200° C. in a laboratory flask with an agitation unit in an oil bath after addition of 30 mg Sn(IV)-octoate at 20 mbar (a). The resulting vapour phase is condensed out and comprises up to over 90% dilactide. After 2.5 hours, 80% of the polycondensate is converted into dilactide. The resulting residue has an average molecular weight of 2,500 g/mol and is converted at 120° C. into the solid state, the racemisation degree in the dilactide phase is 2.5%.

100 g of the thus obtained residue is heated with 50 g hydrolysis medium (90% lactic acid in aqueous solution) at 100° C. and atmospheric pressure for 4 hours with reflux and continuous thorough mixing. The resulting solution is mixed with sodium sulphide and, after 30 min thorough mixing, is filtered in order to remove solid material particles. The thus obtained, homogeneous solution has a lactic acid proportion of over 99% by weight and a racemisation degree of 2.5% and can be mixed with polycondensate in order to supply it directly to the depolymerisation unit. The total racemisation degree of the dilactide obtained after a plurality of cycles never rises, despite the recycling, above the maximum value which is achieved during direct depolymerisation up to a conversion of 95% (see example 1). The total yield is determined by the quantity which is removed during the hydrolysis by separation of the impurities and is preferably above 99%, however in any case more than 95%.

The invention claimed is:

1. A method for the production of cyclic esters of general formula I

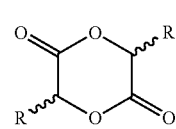

Formula I in which a) in a first step, a part of a mixture of oligomeric carboxylic acids of formula II

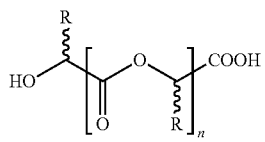

Formula II respectively R being selected, in formulae I to II, from linear or branched aliphatic radicals with 1 to 6 carbon atoms and, in formula II, the average value for n being between 2 and 40, is catalytically converted by cyclising depolymerisation into the cyclic diester of general formula I, wherein the catalyst is a tin containing catalyst, wherein the cyclic depolymerisation is implemented at temperatures between 100 and 300° C., and the thereby produced cyclic diester of general formula I is separated, the part of the oligomeric carboxylic acid of formula II, which is not converted into the cyclic diester of general formula I, is made to react to form a residue during the cyclising depolymerisation, which residue comprises a mixture of oligomeric carboxylic acids of formula II with a higher average value for n than the mixture of oligomeric carboxylic acids of formula II fed into the first step,
b) in a second step, the residue obtained in a first step is hydrolysed at pressures between 500 mbar and 2 bar and/or at temperatures between 50 and 300° C. to a mixture of oligomeric carboxylic acids of formula II, the average value for n being between 1 and 20, an alpha-hydroxycarboxylic acid of formula III,

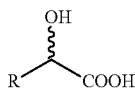

Formula III or a mixture of oligomeric carboxylic acids of formula II with an average value for n between 1 and 20 and an alpha-hydroxycarboxylic acid of formula III, and
c) the hydrolysate obtained in the second step is fed at least partially or completely into the first step,
wherein the cyclising depolymerisation of the first step is implemented until at most 98% by weight of the mixture of oligomeric carboxylic acids of formula II, which is utilized, is converted by the cyclising depolymerisation into the cyclic diester of general formula I.

2. The method according to claim 1, wherein the mixture of oligomeric carboxylic acids of formula II, fed into the first step, is obtained by a preceding polycondensation of an alpha-hydroxycarboxylic acid of formula III.

3. The method according to claim 2, wherein, alternatively or additionally to feeding the hydrolysate into the first step, the hydrolysate is fed partially or completely into the preceding polycondensation of the alpha-hydroxycarboxylic acid of formula III.

4. The method according to claim 1, wherein the cyclising depolymerisation of the first step is implemented until at most 95% by weight of the mixture of oligomeric carboxylic acids of formula II, which is utilized, is converted by the cyclising depolymerisation into the cyclic diester of general formula I.

5. The method according to claim 1, wherein the partial hydrolysis of the residue implemented in the second step is implemented by conversion of the residue with a hydrolysing medium, selected from the group consisting of water, an alpha-hydroxycarboxylic acid of formula III or mixtures of water and an alpha-hydroxycarboxylic acid of formula III.

6. The method according to claim 1, wherein the hydrolysate is purified before recycling, by filtration, nanofiltration, centrifugation, distillation, precipitation and/or separation of the catalyst, ion exchange method or a plurality of the previously mentioned purification methods.

7. The method according to claim 1, wherein the cyclic depolymerisation and/or separation of the cyclic diester of general formula I, produced in the first step, is implemented at pressures which are reduced relative to normal conditions.

8. The method according to claim 1, wherein the stereocentres in formula II have up to at least 95% S-configuration or R-configuration.

9. The method according to claim 8, wherein
a) the stereocentres in formula II have up to at least 95% S-configuration and the cyclising depolymerisation of the first step is implemented until at most 10% of the separated cyclic diester of general formula I has R,S-configuration and/or R,R-configuration, or
b) the stereocentres in formula II have up to at least 95% R-configuration, and the cyclising depolymerisation of the first step is implemented until at most 10% of the separated cyclic diester of general formula I has R,S-configuration and/or S,S-configuration.

10. The method according to claim 8, wherein the hydrolysis implemented in the second step is implemented until a maximum racemisation of 10% relative to the stereocentres of the residue, is effected.

11. The method according to claim 1, wherein R in formulae I to III is methyl.

12. The method according to claim 2, wherein the cyclising depolymerisation of the first step is implemented until at most 95% by weight of the mixture of oligomeric carboxylic acids of formula II, which is utilized, is converted by the cyclising depolymerisation into the cyclic diester of general formula I.

13. The method according to claim 12, wherein the cyclising depolymerisation of the first step is implemented until from 50 to 95% by weight of the mixture of oligomeric carboxylic acids of formula II, which is utilized, is converted by the cyclising depolymerisation into the cyclic diester of general formula I.

14. The method according to claim 2, wherein the partial hydrolysis of the residue implemented in the second step is implemented by conversion of the residue with a hydrolysing medium, selected from the group consisting of water, an alpha-hydroxycarboxylic acid of formula III or mixtures of water and an alpha-hydroxycarboxylic acid of formula III.

15. The method according to claim 2, wherein the hydrolysate is purified before recycling, by filtration, nanofiltration, centrifugation, distillation, precipitation and/or separation of the catalyst, ion exchange method or a plurality of the previously mentioned purification methods.

* * * * *